(12) United States Patent
Rauscher et al.

(10) Patent No.: US 9,418,499 B2
(45) Date of Patent: Aug. 16, 2016

(54) METHOD FOR CHECKING VALUE DOCUMENTS

(75) Inventors: Wolfgang Rauscher, Parkstetten (DE); Jorg Frankenberger, Markt Schwaben (DE)

(73) Assignee: GIESECKE & DEVRIENT GMBH, Munich (DE)

( * ) Notice: Subject to any disclaimer, the term of this patent is extended or adjusted under 35 U.S.C. 154(b) by 277 days.

(21) Appl. No.: 14/110,364

(22) PCT Filed: Apr. 4, 2012

(86) PCT No.: PCT/EP2012/001495
§ 371 (c)(1),
(2), (4) Date: Oct. 7, 2013

(87) PCT Pub. No.: WO2012/136363
PCT Pub. Date: Oct. 11, 2012

(65) Prior Publication Data
US 2014/0125968 A1     May 8, 2014

(30) Foreign Application Priority Data

Apr. 8, 2011   (DE) .......................... 10 2011 016 509

(51) Int. Cl.
*G07D 7/12*     (2016.01)
*G01J 3/28*     (2006.01)
*G01N 21/86*    (2006.01)

(52) U.S. Cl.
CPC . *G07D 7/122* (2013.01); *G01J 3/28* (2013.01); *G01N 21/86* (2013.01)

(58) Field of Classification Search
CPC .............. G01J 3/28; G07D 7/12; G07D 7/122
USPC ........ 250/338.1, 252.1, 458.1, 459.1; 356/71, 356/303, 388, 395, 433, 448; 702/85; 194/302; 382/130–140; 283/72
See application file for complete search history.

(56) References Cited

U.S. PATENT DOCUMENTS

| | | |
|---|---|---|
| 5,027,415 A | 6/1991 | Hara et al. |
| 6,040,584 A | 3/2000 | Liu et al. |

(Continued)

FOREIGN PATENT DOCUMENTS

| | | |
|---|---|---|
| CN | 1831515 A | 9/2006 |
| CN | 101413883 A | 4/2009 |

(Continued)

OTHER PUBLICATIONS

Chinese Search Report from Chinese Application No. 2012800157153, Mar. 24, 2015.

(Continued)

*Primary Examiner* — Marcus Taningco
*Assistant Examiner* — Gisselle Gutierrez
(74) *Attorney, Agent, or Firm* — Workman Nydegger (57) ABSTRACT

The invention relates to a method for checking value documents by which the similarity of the intensity spectrum of a value document to be checked to a reference spectrum can be tested. To check the similarity of the intensity spectrum recorded from the value document to be checked to the reference spectrum, not the recorded intensity spectrum itself is compared with the reference spectrum, but rather a corrected intensity spectrum adapted to the reference spectrum, which arises from the recorded intensity spectrum by a linear correction. The correction parameters of the linear correction function are ascertained by adapting the linearly corrected intensity spectrum to the reference spectrum. Through the adapting it is achieved that fluctuations of the recorded intensity spectrum that are due to measuring technology are compensated at least partly.

15 Claims, 3 Drawing Sheets

(56) References Cited

U.S. PATENT DOCUMENTS

| | | | | |
|---|---|---|---|---|
| 6,937,322 B2* | 8/2005 | Gerz | G07D 7/122 | 250/338.1 |
| 8,212,205 B2* | 7/2012 | Giering | G07D 7/122 | 250/271 |
| 8,300,916 B2 | 10/2012 | Strong | | |
| 9,031,307 B2* | 5/2015 | Giering | G07D 7/122 | 382/137 |
| 2006/0140468 A1 | 6/2006 | Holl | | |
| 2006/0153437 A1* | 7/2006 | Rauscher | G07D 7/002 | 382/135 |
| 2006/0251320 A1 | 11/2006 | Diederichs et al. | | |
| 2007/0095891 A1* | 5/2007 | Giering | G07D 7/12 | 235/379 |
| 2008/0135780 A1* | 6/2008 | Giering | G07D 7/122 | 250/459.1 |
| 2009/0002709 A1 | 1/2009 | Slama | | |
| 2009/0051158 A1* | 2/2009 | Scholz | B42D 25/29 | 283/92 |
| 2009/0074229 A1* | 3/2009 | Giering | G07D 7/122 | 382/100 |
| 2011/0188729 A1 | 8/2011 | Strong | | |
| 2012/0293790 A1* | 11/2012 | Frankenberger | G06K 9/00046 | 356/51 |
| 2013/0214144 A1* | 8/2013 | Hannemann | G01T 1/17 | 250/252.1 |

FOREIGN PATENT DOCUMENTS

| | | |
|---|---|---|
| CN | 101988894 A | 3/2011 |
| DE | 10243051 A1 | 3/2004 |
| DE | 10256114 A1 | 6/2004 |
| DE | 10314071 B3 | 9/2004 |
| EP | 2009600 A2 | 12/2008 |
| EP | 2284806 A2 | 2/2011 |

OTHER PUBLICATIONS

Naes, T., et al., "A User-Friendly Guide to Multivariate Calibration and Classification", NIR Publications, 2002, S. 114-125 und S. 177-187.

Search Report from corresponding German Application No. 10 2011 016 509.6, Jan. 25, 2012.

International Search Report from corresponding PCT Application No. PCT/EP2012/001495, May 21, 2012.

* cited by examiner

METHOD FOR CHECKING VALUE DOCUMENTS

BACKGROUND

This invention relates to a method for checking value documents and to a sensor and an apparatus that carry out the method.

SUMMARY

Value documents are usually checked for authenticity or also for their state, or the type of the respective value document is determined. The check of the value documents is effected in an apparatus for value-document processing which, depending on the value-document properties to be checked, contains one or several sensors which detect different properties of the value documents. Upon the check the value documents are usually checked by optical sensors which detect the light emanating from the value document. In so doing, the value document is usually moved relative to the optical sensor. Such methods are employed for checking value documents such as e.g. bank notes, checks, identity cards, credit cards, check cards, tickets, vouchers and the like.

For checking the authenticity of value documents, methods are known wherein the remission of a value document to be checked is compared with that of an authentic value document. For this purpose it is possible e.g. to compare the remitted intensity of the value document to be checked with that of an authentic value document for one or several certain wavelengths. If the differences are too great in comparison to the authentic value document, the checked value document is classified as false.

An optical check of the value documents is also carried out to subject the newly manufactured value documents to a quality check before their delivery by the manufacturer of the value documents. Here it is tested for example whether the printed image of the value document meets certain specifications. For this optical check there is usually employed an image sensor which detects in three color channels the light remitted by the value document in order to respectively record an image of the value document, e.g. in the red, green and blue spectral regions. If the recorded images do not correspond to the desired printed image in one of the checked value documents, the value document is sorted out in the course of the quality check. However, the quality check of value documents has hitherto not involved any spectrally resolved optical testing of the value documents.

An object of the present invention is hence to state a method for checking the similarity between the intensity spectra of value documents to be checked and a reference spectrum, by which value documents with an acceptable intensity spectrum and value documents with an unacceptable intensity spectrum can be reliably distinguished from each other.

This object is achieved by the subject matter of the independent claims. Claims dependent thereon state advantageous developments and embodiments of the invention.

The method according to the invention involves testing the similarity of the intensity spectrum of a value document to be checked with a reference spectrum. The intensity spectrum whose similarity with a reference spectrum is checked is e.g. a remission spectrum, transmission spectrum or luminescence spectrum of the value document. For recording the intensity spectrum of the value document, the light emanating from the value document is detected at several different wavelengths. To check the similarity of the intensity spectrum recorded from the value document to be checked with the reference spectrum, not the recorded intensity spectrum itself is compared with the reference spectrum, but rather a corrected intensity spectrum adapted to the reference spectrum and arising from the recorded intensity spectrum through a linear correction. The correction parameters of the (linear) correction function are not predetermined, however, but are ascertained through the adapting of the linearly corrected intensity spectrum to the reference spectrum. The adapting using the linear correction function leads to a slight shifting and/or stretching of the recorded intensity spectrum. Through the adapting of the linearly corrected intensity spectrum to the reference spectrum it is achieved that fluctuations of the detected intensities of the recorded intensity spectrum that are due to measuring technology, which are not predictable for the value document to be checked or are not available upon the check of the value document, are compensated at least partly.

For this purpose, the following steps are carried out: The recorded intensity spectrum is corrected using a linear correction function. The linear correction function employs a first correction parameter a and a second correction parameter c. The values of the correction parameters a, c that are necessary for the correction are initially unknown and only ascertained in the course of the adapting. Using the linear correction function there is formed from the recorded intensity spectrum $S(\lambda)$ a corrected intensity spectrum $S'(c, a, \lambda) = c + a \cdot S(\lambda)$. The corrected intensity spectrum $S'(c, a, \lambda) = c + a \cdot S(\lambda)$ is adapted to the reference spectrum in order to reduce a deviation, defined by a distance measure, which the corrected intensity spectrum $S'(c, a, \lambda)$ has from the reference spectrum $R(\lambda)$. In particular, this deviation can be minimized through the adapting. The first and second correction parameters are independent of the wavelength $\lambda$, i.e. the same first correction parameter c and the same second correction parameter a are employed for all wavelengths. It is thereby achieved that the corrected intensity spectrum is not falsified over the recorded intensity spectrum.

The deviation, defined by a distance measure, of the corrected intensity spectrum from the reference spectrum results by calculating a distance measure for the intensity differences, present at different wavelengths, of the corrected intensity spectrum $S'(c, a, \lambda)$ from the reference spectrum $R(\lambda)$. The distance measure is e.g. the Euclidean distance, the Manhattan distance, the chessboard distance or another mathematical distance of the corrected intensity spectrum $S'(c, a, \lambda)$ from the reference spectrum $R(\lambda)$. The adapting of the corrected intensity spectrum $S'(c, a, \lambda)$ to the reference spectrum $R(\lambda)$ is preferably effected by a least-squares fit. However, the corrected intensity spectrum $S'(c, a, \lambda) = c + a \cdot S(\lambda)$ can also be adapted to the reference spectrum iteratively, e.g. by varying the correction parameters a and c.

The result of the adaptation is a corrected intensity spectrum $S'(\lambda) = c^* + a^* \cdot S(\lambda)$ adapted to the reference spectrum, its first correction parameter being $c^*$ and its second correction parameter being $a^*$, where $c^*$ and $a^*$ represent concrete numerical values which are independent of the wavelength $\lambda$, i.e. are the same for all wavelengths. The deviation, defined by the distance measure, of the corrected intensity spectrum from the reference spectrum is at $c = c^*$ and $a = a^*$ hence reduced in comparison to the deviation, defined by the distance measure, which the recorded intensity spectrum has from the reference spectrum, or even assumes a minimum. For the adapted corrected intensity spectrum $S'(\lambda) = c^* + a^* \cdot S(\lambda)$ ascertained in this way, there is subsequently calculated a distance that the adapted corrected intensity spectrum $S'(\lambda) = c^* + a^* \cdot S(\lambda)$ has from the reference spectrum. The calculated distance is employed for assessing the similarity between the recorded intensity spectrum $S(\lambda)$ and the reference spectrum $R(\lambda)$.

Upon adapting, the correction parameters a and c are for example varied until the deviation defined by the distance measure reaches a minimum, i.e. until a further variation of the correction parameters a and c no longer causes a reduction of the deviation defined by the distance measure. If the deviation, defined by the distance measure, which the corrected intensity spectrum has from the reference spectrum is minimized upon adapting, there is employed the adapted corrected intensity spectrum $S'(\lambda)=c^*+a^*\cdot S(\lambda)$ whose deviation from the reference spectrum $R(\lambda)$ is minimal. However, the adapting can also be terminated if the deviation defined by the distance measure is smaller than a certain threshold value.

The adapting of the corrected intensity spectrum to the reference spectrum and the employment of the corrected intensity spectrum $S'(\lambda)=c^*+a^*\cdot S(\lambda)$ adapted to the reference spectrum for calculating the distance make it possible to at least partly compensate fluctuations due to measuring technology which have influenced the intensity spectrum $S(\lambda)$ upon its recording. These include e.g. inaccuracies of the detection site on the value document (due e.g. to transport fluctuations of the value document), which can change the recorded intensity spectrum in the case of inhomogeneous spectral properties of the value document. Value documents with unacceptable intensity spectra can be reliably distinguished from value documents with acceptable intensity spectra on the basis of the adapting.

Upon the adapting of the corrected intensity spectrum $S(\lambda)$, the first and second correction parameters a* and c* for which the deviation, defined by the distance measure, of the adapted corrected intensity spectrum $S'(\lambda)=c^*+a^*\cdot S(\lambda)$ from the reference spectrum $R(\lambda)$ is reduced or minimal are ascertained individually for each single value document to be checked. In contrast to a non-individual adaptation to the reference spectrum (employing the same correction parameters c* and a* for several recorded intensity spectra), a much better adaptation is thereby obtained. If several intensity spectra are to be tested for similarity to the reference spectrum for the value document to be checked, the adapting can be also be carried out individually for each single intensity spectrum $S(\lambda)$ of the value document to be checked.

The adapting of the corrected intensity spectrum $S'(c, a, \lambda)$ to the reference spectrum $R(\lambda)$ is carried out e.g. within the framework of a compensation calculation which corresponds to a fitting of the corrected intensity spectrum $S'(c, a, \lambda)$ to the reference spectrum $R(\lambda)$ using the fit parameters a and c. The compensation calculation is e.g. a least-squares fit of the corrected intensity spectrum $S'(c, a, \lambda)$ to the reference spectrum $R(\lambda)$ or is at least based on such a fit. In the case of a least-squares fit, there is calculated upon adapting as the deviation the average square deviation of the corrected intensity spectrum from the reference spectrum. The least-squares fit is advantageous because it requires little computing time and hence enables a similarity assessment in real time for each checked value document, even during a high-speed check of the value documents.

For the calculation of the deviation defined by the distance measure within the framework of the adaptation, on the one hand, and the calculation of the distance (employed for the similarity assessment) of the adapted corrected intensity spectrum $S'(\lambda)=c^*+a^*\cdot S(\lambda)$ from the reference spectrum $R(\lambda)$, on the other hand, the same distance measure can be employed. However, it is preferable to employ as the distance for the similarity assessment the chessboard distance $\|S'(\lambda)-R(\lambda)\|\infty$ of the adapted corrected intensity spectrum $S'(\lambda)=c^*+a^*\cdot S(\lambda)$ from the reference spectrum $R(\lambda)$, said distance being the maximal difference between $S'(\lambda)=c^*+a^*\cdot S(\lambda)$ and $R(\lambda)$ that is present between the two intensity spectra at any one of the contemplated wavelengths $\lambda$.

The calculated distance is employed e.g. as a similarity measure that enables a quantitative statement of the similarity of the recorded intensity spectrum with the reference spectrum. For assessing the similarity between the intensity spectrum $S(\lambda)$ recorded from the value document and the reference spectrum $R(\lambda)$, the calculated distance can be compared with one or several threshold values. When the distance exceeds the threshold value for one or several detection sites on the value document, the checked value document is assigned an accordingly low degree of similarity and the value document is sorted out, where applicable.

The assessment of the similarity between the recorded intensity spectrum of the value document and the reference spectrum is carried out e.g. within the framework of the quality check of the value documents before their delivery. The method according to the invention enables a spectral characteristic of a security feature of the value document to be checked for its similarity with a spectral characteristic specified for the security feature with which the security feature was specified before its application or incorporation into the value document. The distance can be employed here as a similarity measure for the quality check of the security feature. The security feature whose spectral characteristic is checked is e.g. a special printing ink applied to the value document and identified by a specified spectral characteristic. It is especially advantageous here to employ the chessboard distance as the distance, because it can be compared directly with the fluctuation range with which the security feature, in particular the printing ink, was specified before the value document was equipped with the security feature.

The adapting of the corrected intensity spectrum $S'(c, a, \lambda)$ to the reference spectrum $R(\lambda)$ can be carried out for the entire spectral region of the recorded intensity spectrum or for one or for several spectral portions of the same. Upon adapting there can also be calculated the deviation defined by the distance measure that the corrected intensity spectrum has from the reference spectrum, averaged over several spectral regions mutually separated spectrally. An optimal adaptation is obtained when the adapting is carried out for a spectral portion that completely comprises the spectral characteristic of the security feature and that extends beyond the spectral portion in which the spectral characteristic lies. If the spectral characteristic lies in the infrared, the corrected intensity spectrum is preferably adapted to the reference spectrum in a spectral portion of the recorded intensity spectrum that lies completely in the infrared, no account being taken, upon adapting, of a spectral portion of the recorded intensity spectrum lying in the visible, if any. The spectral portion in the infrared for which the adapting is carried out preferably comprises only wavelengths over 800 nm. Through the adapting only in the infrared it is achieved that the same reference spectrum is employable for several visible printing inks that respectively contain the same security feature. The effort that would arise from handling individual reference spectra for each single type of value document can thereby be avoided.

The distance of the adapted corrected intensity spectrum from the reference spectrum, which distance is employed for assessing similarity, is preferably calculated only for the spectral portion for which the corrected intensity spectrum was adapted to the reference spectrum, or for a partial portion of the same. In particular, the distance is calculated only for a spectral portion of the adapted corrected intensity spectrum over which the spectral characteristic of the value document's security feature to be checked extends. Said portion preferably lies completely in the infrared.

So as not to falsify the adapted corrected intensity spectrum $S'(\lambda)$ in comparison with the recorded intensity spectrum $S(\lambda)$, a constrained adapting of the corrected intensity spectrum to the reference spectrum $R(\lambda)$ can be carried out. In order for a falsifying of the intensity spectrum to be excluded upon adapting, certain conditions are prescribed for the first and second correction parameters. To obtain a constrained adapting, one or several certain side conditions are prescribed e.g. for two parameters $w=1/(a^*+c^*)$ and $s=a^*/(a^*+c^*)$ derived from the first and second correction parameters $a^*$, $c^*$. A possible side condition is that the derived parameters w, s are interdependent such that they satisfy a certain mathematical relation. However, adapting can also be constrained by the side condition that the parameters w, s respectively lie within certain limits, in particular that w lies in a values range [w1, w2] lying around 1, and s in a values range [s1, s2] lying around 1, where it preferably holds that $0.8<w1<1.1<w2<1.2$, $0.8<s1<1.1<s2<1.2$. The values ranges for w and s can in certain cases also not lie around 1, however, but around a greater or smaller numerical value. The constraint is advantageous if the method according to the invention is mistakenly applied to other value documents for which the reference spectrum $R(\lambda)$ underlying the method is not valid. For the intensity spectra of such value documents could otherwise be falsified by the (unconstrained) adapting.

By the constrained adapting it is achieved that the spectral shape of the recorded intensity spectrum $S(\lambda)$, in particular its spectral characteristic, is substantially retained upon adapting. The adapted corrected intensity spectrum hence has substantially the same spectral characteristic as the recorded intensity spectrum. The constrained adapting leads at most to a slight shifting and/or stretching of the recorded intensity spectrum.

For constrained adapting of the corrected intensity spectrum $S'(c, a, \lambda)$ to the reference spectrum $R(\lambda)$, there are carried out for example, after the adapting step, the following steps:

determining the first correction parameter $c^*$ and the second correction parameter $a^*$ of the adapted corrected intensity spectrum $S'(\lambda)$ for which the deviation, defined by the distance measure, of the adapted corrected intensity spectrum $S'(\lambda)$ from the reference spectrum $R(\lambda)$ is reduced or minimal, calculating the parameter $w=1/(a^*+c^*)$ and the parameter $s=a^*/(a^*+c^*)$, checking whether the parameter w lies in a predetermined interval $[w_1, w_2]$ around 1 and whether the parameter s lies in a predetermined interval $[s_1, s_2]$ around 1, constraining the parameter w to $w_1$ if $w<w_1$ and to $w_2$ if $w>w_2$, and constraining the parameter s to $s_1$ if $s<s_1$ and to $s_2$ if $s>s_2$, employing the constrained parameter $w=w_1$ or $w=w_2$ and/or the constrained parameter $s=s_1$ or $s=s_2$ for determining a constrained-adapted corrected intensity spectrum $S_B'(\lambda)=c^*+a^*\cdot S(\lambda)$ whose first correction parameter is $c^*=(1-s)/w$ and whose second correction parameter is $a^*=s/w$, calculating a distance (A) which the constrained-adapted corrected intensity spectrum $S_B'(\lambda)$ has from the reference spectrum $R(\lambda)$, employing the calculated distance (A) for assessing the similarity between the intensity spectrum $S(\lambda)$ recorded from the value document and the reference spectrum $R(\lambda)$.

The invention moreover relates to a sensor which is configured for carrying out the method. The sensor records the intensity spectrum of the value document to be checked. For this purpose, the sensor has measuring elements for spectrally resolved detection of the light emanating from the value document to be checked, e.g. one or several light sources which are spectrally different, where applicable, one or several dispersive elements, where applicable, and one or several detection devices. The sensor is moreover equipped with an evaluation device which applies the steps of the method according to the invention to the recorded intensity spectrum of the value document. For carrying out these steps, the sensor is equipped with corresponding hardware and/or programmed with corresponding software. The sensor is installed e.g. in an apparatus for checking value documents which has a transport system through which the value documents to be checked are transported singly one after the other past the sensor which checks the value documents.

Before the onset of the method according to the invention, the reference spectrum respectively suitable for this value document can be selected manually or automatically, e.g. by corresponding adjustment on the apparatus or on the sensor which carries out the method. The selected reference spectrum can be valid for different types of value documents. The information about which reference spectrum is suitable for the value document can also be obtained by an automatic recognition of the value document, e.g. on the basis of measurements on the value document which are carried out on-line with the method according to the invention.

BRIEF DESCRIPTION OF THE DRAWINGS

Hereinafter the invention will be explained by way of example with reference to the following figures. There are shown.

DETAILED DESCRIPTION OF VARIOUS EMBODIMENTS

The method according to the invention can be used in general for testing the similarity of intensity spectra. The intensity spectrum whose similarity to a reference spectrum is checked is e.g. a remission spectrum, transmission spectrum or luminescence spectrum of the value document. Such a similarity test can be used e.g. for authenticity checking, for checking the state or the type or other properties of the value document. Hereinafter the method according to the invention will be described by the example of the quality check of value documents which are to be checked for the presence of a security feature after their manufacture. In so doing it is checked whether the intensity spectrum of the respective value document has a sufficient similarity to a certain spectral characteristic.

Figure 1A:
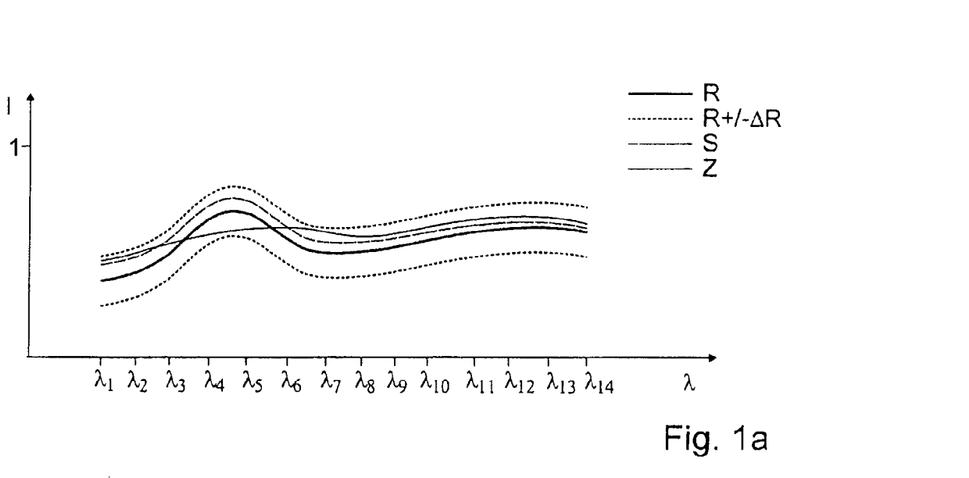
FIG. 1a Examples of recorded intensity spectra $S(\lambda)$, $Z(\lambda)$ in comparison with a reference spectrum $R(\lambda)$ with the acceptance interval $R(\lambda)+/-\Delta R$, FIG. 1b Examples of recorded intensity spectra $S_i(\lambda)$ of a multiplicity of value documents in comparison with the reference spectrum $R(\lambda)$ with the acceptance interval $R(\lambda)+/-\Delta R$, FIG. 2a The intensity spectrum $S(\lambda)$ from FIG. 1a and the corrected intensity spectrum SP) adapted to the reference spectrum $R(\lambda)$, whose deviation from the reference spectrum $R(\lambda)$ is minimal, FIG. 2b The corrected intensity spectra $S_i'(\lambda)$ adapted to the reference spectrum $R(\lambda)$ from FIG. 1b in comparison with the acceptance interval $R(\lambda)+/-\Delta R$ around the reference spectrum $R(\lambda)$ and in comparison with a reduced acceptance interval $R(\lambda)+/-\delta R$, FIG. 2c The intensity spectra $Z(\lambda)$, $Z'(\lambda)$ in comparison with the acceptance interval $R(\lambda)+/-\Delta R$ around the reference spectrum $R(\lambda)$ and in comparison with the reduced acceptance interval $R(\lambda)+/-\delta R$, FIG. 3a Parameters s and w ascertained upon the adapting of different intensity spectra, and their constraint to the interval $[s_1, s_2]$ and $[w_1, w_2]$, FIG. 3b Example of the constrained adaptation of an intensity spectrum $Y(\lambda)$.

In FIG. 1$a$ there is shown as an intensity spectrum $S(\lambda)$ the remission spectrum of a value document to be checked, which was recorded by detecting light from the value document at different wavelengths. The intensity spectrum can be a continuous intensity spectrum which was obtained by spectrally resolved detecting of the light emanating from the value document in the range $\lambda 1$ to $\lambda 14$. Alternatively, however, the intensity spectrum can also be formed from individual discrete intensity values, e.g. at the wavelengths $\lambda 1$ to $\lambda 14$, cf. FIG. 1$a$. Further, the intensity spectrum can be recorded from a certain detection site on the value document or be an intensity spectrum averaged over several detection sites within a certain region (ROI) on the value document. The intensity spectrum can consist of the absolute intensity values, e.g. of the intensities detected by a detector at different wavelengths, after a correction due to the spectral sensitivity of the detector, where applicable, and based on the irradiated light intensity with which the value document is illuminated, where applicable. In the following example, however, intensity spectra consisting of relative intensity values will be contemplated, i.e. the intensities detected at different wavelengths have been based on a base (or reference) intensity of the value document (e.g. an intensity detected in the white field of the value document), e.g. by forming the ratio to the base intensity.

FIG. 1$a$ moreover shows a reference spectrum $R(\lambda)$ with which the recorded intensity spectrum $S(\lambda)$ is to be compared. As a reference spectrum there is employed e.g. a target spectrum which is ideally expected from the value document. The reference spectrum $R(\lambda)$ is e.g. a reference spectrum specific to the respective detection site or ROI, or a reference spectrum expected for the value document as a whole. The comparison with the reference spectrum $R(\lambda)$ is effected by testing whether the recorded intensity spectrum $S(\lambda)$ lies in an acceptance range around the reference spectrum $R(\lambda)$. Thus, FIG. 1$a$ indicates the limits of a possible acceptance range, which in this example are given by two spectra $R(\lambda)+\Delta R$ and $R(\lambda)-\Delta R$ shifted parallel to the reference spectrum $R(\lambda)$, at a fixed distance $\Delta R$ above and below the reference spectrum $R(\lambda)$. The test of whether the intensity spectrum $S(\lambda)$ lies in the acceptance range $R(\lambda)+/-\Delta R$ is carried out e.g. within the framework of a quality check of the value documents. The value document with the intensity spectrum $S(\lambda)$ would be accepted upon the quality check, because it lies within the acceptance range.

Figure 1B:
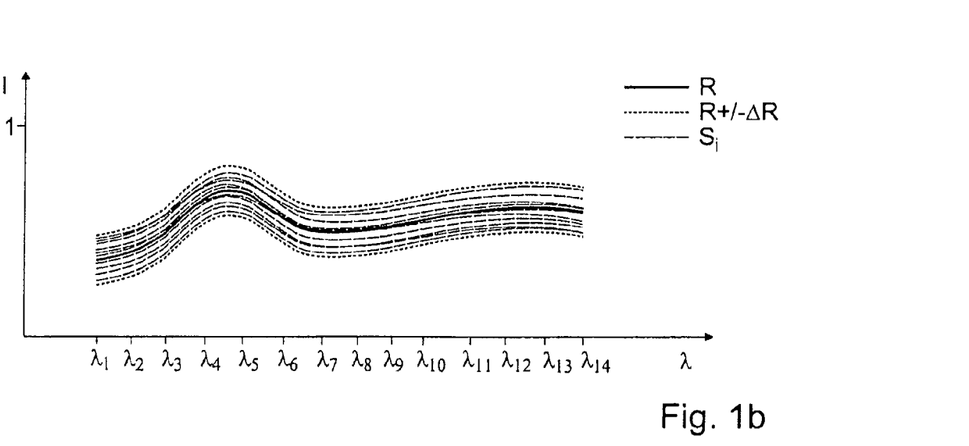

FIG. 1$b$ shows a multiplicity of intensity spectra $Si(\lambda)$ (with $i=1, 2, \ldots n$) which were recorded from a multiplicity n of different value documents. For these n value documents, a spectral characteristic corresponding to the reference spectrum is also expected. With regard to a quality check using the acceptance range $R(\lambda)+/-\Delta R$, all these n value documents show an acceptable spectral characteristic. However, the individual intensity spectra $Si(\lambda)$ differ from each other for various reasons:

Firstly, the spectral properties of the value documents to be checked deviate slightly from each other on account of unavoidable fluctuations during manufacture of the value documents. Within the framework of the quality check these fluctuations are to be tested.

Secondly, spectral differences of the intensity spectra $Si(\lambda)$ of the different value documents also result due to measuring technology. The spectral properties of a value document usually vary in dependence on the detection site on the value document, e.g. due to colors (or inks) or security features applied locally, only in certain regions of the value document, or due to the print design which results in an inhomogeneous areal application or an inhomogeneous area coverage of the imprinted color. If the actual detection site on the respective value document on which the intensity spectrum is recorded does not exactly match the target detection site for which the reference spectrum holds, this can lead to deviations of the recorded intensity spectrum from the reference spectrum, due to the locally varying spectral properties of the value document. Such fluctuations of the detection site occur e.g. due to a positioning inaccuracy of the value document or due to transport fluctuations of the value document when the value document, for its checking, is transported by a transport system past a sensor which records the intensity spectrum. With the intensity spectra $Si(\lambda)$ of FIG. 1$b$, primarily the fluctuations of the detection site are responsible for the deviations of the intensity spectra $Si(\lambda)$ from the reference spectrum $R(\lambda)$.

Thirdly, the intensity spectra of the checked value documents can also vary due to the relative measurement of the detected intensities when the intensity detected at the detection site is based on the intensity detected in the base (or reference) region of the respective value document. When the base regions of the checked value documents differ from each other in their opacity, have soiling or when different watermarks are present in the base regions of different value documents, this leads to slight fluctuations of the base intensity, which likewise leads to a change of the recorded intensity spectra.

Because the intensity spectra $Si(\lambda)$ of all n value documents have an acceptable spectral characteristic, all these n value documents should be accepted upon the quality check. Therefore, the acceptance range $R(\lambda)+/-\Delta R$ was chosen so large that these n value documents are not rejected upon the quality check. On the other hand, the large acceptance range $R(\lambda)+/-\Delta R$ has the consequence, however, that value documents with an unacceptable intensity spectrum, such as e.g. the intensity spectrum $Z(\lambda)$ from FIG. 1$a$, would also be accepted upon the quality check. The intensity spectrum $Z(\lambda)$ was recorded from another value document which should have a spectral characteristic corresponding to the reference spectrum $R(\lambda)$ but upon whose manufacture an error occurred. Due to the error the spectrum $Z(\lambda)$ shows a different spectral characteristic from the reference spectrum $R(\lambda)$ and from the intensity spectrum $S(\lambda)$. Because the spectrum $Z(\lambda)$ of the other value document nevertheless lies within the acceptance range $R(\lambda)+/-\Delta R$, however, the other value document would also be accepted.

Figure 2A:
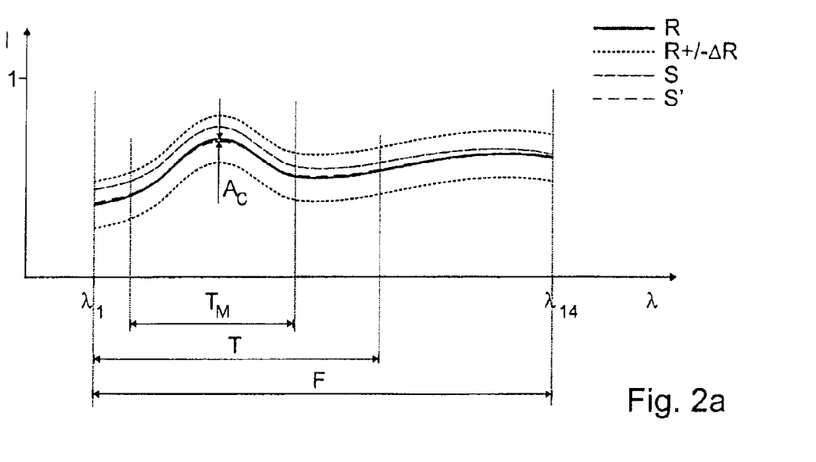

FIG. 2$a$ illustrates the method according to the invention by the example of the intensity spectrum $S(\lambda)$. The intensity spectrum $S(\lambda)$ is adapted to the reference spectrum $R(\lambda)$ here using a linear correction. For this purpose, there is first calculated from the intensity spectrum $S(\lambda)$ a corrected intensity spectrum $S'(c, a, \lambda)=c+a \cdot S(\lambda)$, which is the linear transform of the recorded intensity spectrum $S(\lambda)$ and which depends on the first correction parameter c and on the second correction parameter a, which are independent of the wavelength $\lambda$. By a compensation calculation, e.g. a least-squares fit, there are ascertained the two correction parameters $c^*$, $a^*$ for which the deviation of the linearly corrected intensity spectrum from the reference spectrum (which is defined by the chosen distance measure) is minimal.

The compensation calculation can also be carried out iteratively. For the first correction parameter c and the second correction parameter a, there are then first used initial values c0 and a0, e.g. c0=0 and a0=1. Starting out from c0 and a0, c and a are iteratively varied, the appurtenant corrected intensity spectrum $S'(c, a, \lambda)=c+a\cdot S(\lambda)$ is respectively determined, and the deviation, defined by the chosen distance measure, of this corrected intensity spectrum $S'(\lambda)=c+a\cdot S(\lambda)$ from the reference spectrum $R(\lambda)$ is respectively calculated. The correction parameters c and a are varied until the deviation, defined by the distance measure, of the corrected intensity spectrum $S'(\lambda)=c+a\cdot S(\lambda)$ from the reference spectrum $R(\lambda)$ reaches a minimum. The result of this adaptation is a certain linearly corrected intensity spectrum $S'(\lambda)=c^*+a^*\cdot S(\lambda)$ with the correction parameters $c^*$ and $a^*$ for which the corrected intensity spectrum $S'(\lambda)$ least deviates from the reference spectrum $R(\lambda)$.

Starting out from the recorded intensity spectrum $S(\lambda)$ there thus results the adapted corrected intensity spectrum $S'(\lambda)$ from FIG. 2a, which was adapted to the reference spectrum $R(\lambda)$ using the compensation calculation. Through the adapting of the intensity spectrum $S(\lambda)$ to the reference spectrum $R(\lambda)$ it is achieved that variations of the detection site or of the base intensities, which are not exactly predictable for the respectively checked value document or which are not available for the evaluation, are compensated at least partly.

The corrected intensity spectrum $S'(\lambda)$ is adapted to the reference spectrum $R(\lambda)$ in a certain spectral region F. For the adaptation of the corrected intensity spectrum $S'(\lambda)$ to the reference spectrum $R(\lambda)$, account is only taken of those intensity values that were detected at wavelengths of the spectral region F, while the intensity values detected outside the spectral region F are left out of account. That is to say, the deviation, defined by the distance measure, of the intensity values detected within the spectral region F from the reference spectrum is minimized.

Figure 2B:
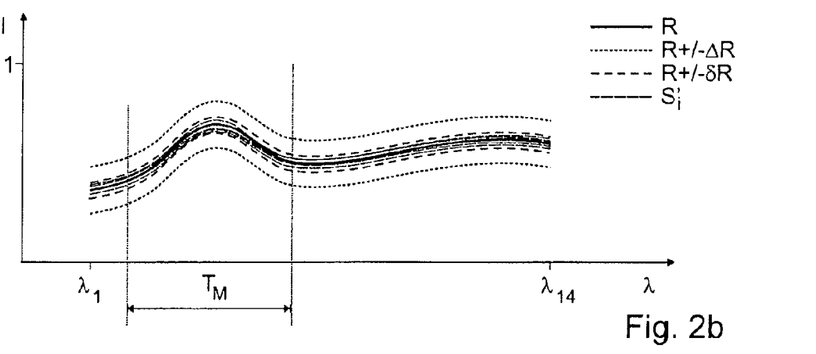

FIG. 2b shows the result of the adaptation for the multiplicity of the intensity spectra $Si(\lambda)$ from FIG. 1b. Each of the intensity spectra $Si(\lambda)$ was adapted to the reference spectrum $R(\lambda)$ individually using the linear correction, with the correction parameters $c^*$, $a^*$ generally assuming different values for the individual adaptations. This results in the corrected intensity spectra $S'i(\lambda)$ represented in FIG. 2b. The corrected intensity spectra $S'i(\lambda)$ deviate from the reference spectrum $R(\lambda)$ considerably less due to the adaptation. For the variation of the detection site or of the base intensities, which caused the fluctuations of the intensity spectra $Si(\lambda)$ from FIG. 1b, was strongly reduced or compensated by the adaptation. Due to the adaptation, a considerably smaller acceptance range $R(\lambda)+/-\delta R$ can hence be employed for the quality check of the value documents. For all n value documents the adapted intensity spectrum $S'i(\lambda)$ lies in this acceptance range $R(\lambda)+/-\delta R$.

Figure 2C:
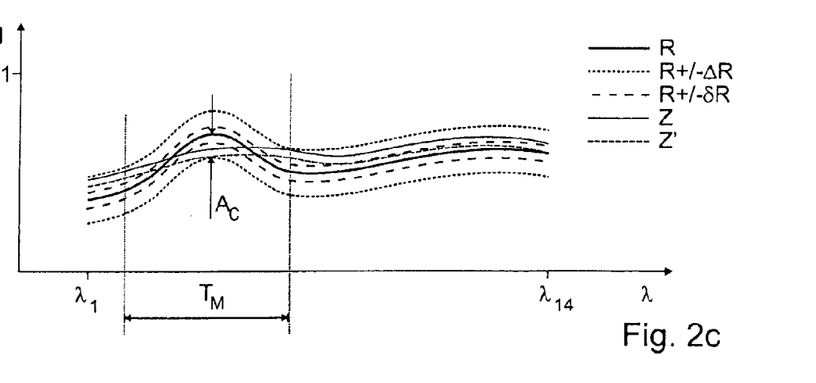

The intensity spectrum of a value document with unacceptable quality, such as e.g. the intensity spectrum $Z(\lambda)$ from FIG. 1a, is also approximated to the reference spectrum $R(\lambda)$ by the adaptation. However, in this case the adaptation only leads to an approximation, not to such a good match with the reference spectrum as in the case of the intensity spectra $Si(\lambda)$. An intensity spectrum $Z'(\lambda)$ adapted to the reference spectrum $R(\lambda)$ would hence, in spite of the adaptation, exceed the limits of the reduced acceptance range $R(\lambda)+/-\delta R$, cf. FIG. 2c. The value document with the unacceptable intensity spectrum $Z(\lambda)$ can thus be reliably distinguished from the value documents with the acceptable intensity spectra $S(\lambda)$ and $Si(\lambda)$.

For the check of the value documents there is carried out a quantitative assessment of the similarity between the intensity spectrum $S(\lambda)$ recorded from the value document and the reference spectrum $R(\lambda)$. As a similarity measure there can be calculated for this purpose the distance that the corrected intensity spectrum $S'(\lambda)$ adapted to the reference spectrum $R(\lambda)$ has from the reference spectrum $R(\lambda)$. For the quality check there is calculated the distance AC that the corrected intensity spectrum $S'(\lambda)$ adapted to the reference spectrum $R(\lambda)$ has from the reference spectrum $R(\lambda)$ in a certain spectral region. This spectral region can be the spectral region F for which the adaptation of the corrected intensity spectrum $S'(\lambda)$ to the reference spectrum $R(\lambda)$ was also carried out. Alternatively, however, the distance AC can also be calculated for a partial portion T of the spectral region F, cf. FIG. 2a. If the quality check is to check the quality of a color or a security feature having a certain spectral characteristic, the distance AC is calculated for the partial portion in which the spectral characteristic is supposed to lie, e.g. for the partial portion TM from FIG. 2a.

The calculated distance AC can be employed directly for the quality check of the value documents. For this purpose, the distance AC can be compared e.g. with a threshold upon whose exceeding the value document is assigned an unacceptable quality. If the calculated distance AC lies below a certain threshold, the value document is assigned an acceptable quality. However, the calculated distance AC can also be taken into account as one of several quality criteria, in connection with other quality criteria. The quality of the value document is rated as acceptable e.g. only if several of the quality criteria are fulfilled simultaneously.

As a distance measure there is employed the chessboard distance $AC=\|S'(\lambda)-R(\lambda)\|\infty$. Said distance corresponds to the greatest intensity difference $|c^*+a^*\cdot S(\lambda)-R(\lambda)|$ between the intensity spectrum $S'(\lambda)$ and the reference spectrum $R(\lambda)$ that exists at any one of the wavelengths $\lambda$ of the contemplated spectral region, cf. FIGS. 2a, 2c, 3b. The chessboard distance AC is advantageous in comparison to other distance measures, such as e.g. in comparison to the average square distance. For the chessboard distance AC that the corrected intensity spectrum has from the reference spectrum $R(\lambda)$ can be compared directly with the maximal fluctuation range $\delta R$ with which colors or security features are usually specified. If the chessboard distance AC amounts to more than the fluctuation range $\delta R$, this is equivalent to the corrected intensity spectrum, at least at one wavelength, exceeding the limits of the acceptance range $R(\lambda)+/-\delta R$ prescribed within the framework of the specification. Because the chessboard distance AC thus corresponds directly with the specification of the color or of the security feature, the chessboard distance AC can be used to check the adherence to the specification in a simple manner. Moreover, the chessboard distance AC is very clear for a person wishing to understand the results of the quality check in comparison to the specification using a graphical representation of the corrected intensity spectrum $S'(\lambda)$ in comparison to the upper limit $R(\lambda)+\delta R$ and lower limit $R(\lambda)-\delta R$. Other distance measures, such as e.g. the average square distance, are less clear in comparison to the chessboard distance, do not correspond directly with what is prescribed by the specification, and hence are not easy to compare with a specified fluctuation range.

In a development of the method, there can be employed as a distance measure a weighted chessboard distance AC, taking as a basis a wavelength-dependent acceptance range $R(\lambda)+/-\delta R(\lambda)$ with a wavelength-dependent width $\delta R(\lambda)$. The weighted chessboard distance is calculated by $AC=\|(S'(\lambda)-R(\lambda)/\delta R(\lambda)\|\infty$.

In the method according to the invention, a constrained adaptation can be carried out to avoid a falsification of the recorded intensity spectra through the adapting. Through the constrained adaptation, the spectral shape of the recorded intensity spectrum is retained upon adapting to the reference spectrum $R(\lambda)$. The adapting is constrained in this example by two parameters $s=a^*/(a^*+c^*)$ and $w=1/(a^*+c^*)$, derived from the first and second correction parameters $a^*$, $c^*$, satisfying the side condition that they lie within certain limits. If the parameter w does not lie in a predetermined interval [w1, w2] around 1 upon unconstrained adapting, it is constrained to $w=w1$ if $w<w1$ and to $w=w2$ if $w>w2$. Accordingly, the parameter s is constrained, if it does not lie in a predetermined interval [s1, s2] around 1 upon unconstrained adapting, to $s=s1$ if $s<s1$ and to $s=s2$ if $s>s2$. If only minimal corrections had to be carried out within the framework of the adaptation, the parameters assume the values $w\approx1$ and $s\approx1$, so that the constraint has no effects on the adapted corrected intensity spectrum.

Figure 3A:
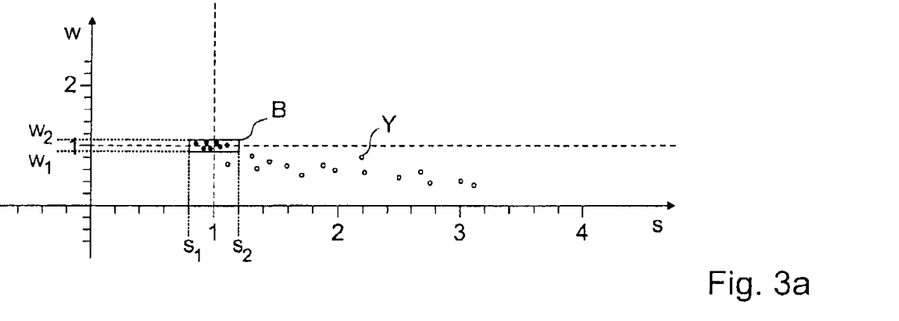

FIG. 3a shows an example of the values range B to which the parameters s and w can be constrained, there being prescribed in this example a values range from 0.8 to 1.2 for s and a values range from 0.9 to 1.1 for w. By constraint of the parameters s, w there is avoided an excessively strong correction of the base intensity underlying the relative measurement of the intensity, and an excessively strong correction of the spectral change that occurs through the fluctuations of the detection site. By the constraint of the values pairs (s, w) to the range B it is achieved that only physically justified influences are corrected that (slightly) change the intensity spectrum. The constrained adapting guarantees that the spectral shape of the corrected intensity spectrum corresponds to that of the respectively recorded intensity spectrum.

In the diagram of FIG. 3a, values pairs (s, w) of the two parameters s and w are plotted for a multiplicity of value documents, with each values pair (s, w) having been ascertained individually by (unconstrained) adapting of the recorded intensity spectrum of a value document to the reference spectrum $R(\lambda)$. For value documents having an acceptable spectral characteristic, there were ascertained values pairs (s, w) lying within the values range B (black dots in FIG. 3a). These include e.g. the value documents 1 to n having the intensity spectra $Si(\lambda)$, where $i=1, 2, \ldots n$. The values pairs (s, w) lying outside the values range B were ascertained for value documents not having the characteristic spectrum (rings in FIG. 3a). Their parameters s and w deviate from $(s, w)=(1, 1)$ so strongly that they exceed the limits of the values range B and are hence limited by the constraint. For example, upon the (unconstrained) adaptation of a recorded intensity spectrum $Y(\lambda)$ of a further value document the parameters $sY=2.2$, $wY=0.8$ were ascertained. Instead of the parameters $(sY, wY)=(2.2, 0.8)$ which the unconstrained adapting of the recorded intensity spectrum $Y(\lambda)$ to the reference spectrum $R(\lambda)$ yielded, the parameters are constrained to $(sY, wY)=(s2, w1)$. From the thus constrained parameter $sY=s2$ and $wY=w1$ there is determined a constrained-adapted corrected intensity spectrum $YB(\lambda)=c^*+a^*\cdot Y(\lambda)$, whose first correction parameter is $c^*=(1-s2)/w1$ and whose second correction parameter is $a^*=s2/w1$. In the example of FIG. 3a, (sY, wY) are constrained to $(s2, w1)=(1.2, 0.9)$.

Figure 3B:
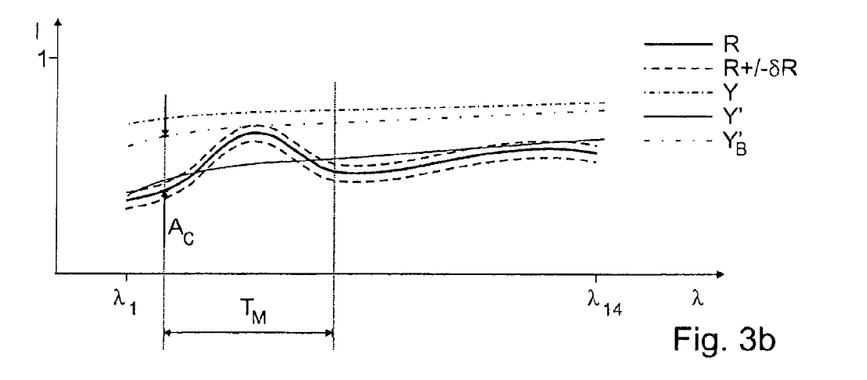

FIG. 3b shows the recorded intensity spectrum $Y(\lambda)$ of the further value document upon whose manufacture insufficient color was mistakenly employed. By the constraint of sY to 1.2 and wY to 0.9 there results the constrained-adapted corrected intensity spectrum $YB'(\lambda)$. Without constraint of the parameters w and s the adapting of the recorded intensity spectrum $Y(\lambda)$ to the reference spectrum $R(\lambda)$ would lead to the intensity spectrum $Y'(\lambda)=(1-s)/w+s/w\cdot Y(\lambda)$, which has a considerably lower deviation from the reference spectrum $R(\lambda)$, cf. FIG. 3b. In comparison to the recorded intensity spectrum $Y(\lambda)$, the intensity spectrum $Y'(\lambda)$ was falsified by the (unconstrained) adapting to the reference spectrum $R(\lambda)$, however. Through the constraint of the parameters w and s to the values range B, the adapting of the spectrum $Y(\lambda)$ to the reference spectrum $R(\lambda)$ leads to the constrained-adapted intensity spectrum $YB'(\lambda)=(1-s2)/w1+s2/w1\cdot Y(\lambda)$, which corresponds substantially to the recorded intensity spectrum $Y(\lambda)$.

Analogously to the case without constraint, there is also calculated in the case of a constrained adaptation the distance AC that the constrained-adapted corrected intensity spectrum $YB'(\lambda)$ has from the reference spectrum $R(\lambda)$, and the calculated distance AC is employed for assessing the similarity between the intensity spectrum recorded from the further value document and the reference spectrum $R(\lambda)$. In the shown example the thus ascertained distance AC of the intensity spectrum $YB'(\lambda)$ is so great that the limits of the reduced acceptance range $R(\lambda)+/-\delta r$ are far exceeded, cf. FIG. 3b. The further value document would hence be assigned an unacceptable quality.

The invention claimed is:

1. A method for checking value documents, comprising the steps of:
    detecting at several different wavelengths the light emanating from a value document for recording an intensity spectrum $S(\lambda)$ of the value document;
    forming a corrected intensity spectrum $S'(c,a,\lambda)=c+a\cdot S(\lambda)$ by correcting the recorded intensity spectrum using a linear correction function, so that the corrected intensity spectrum $S'(c,a,\lambda)=c+a\cdot S(\lambda)$ is a linear transform of the recorded intensity spectrum $S(\lambda)$ and implements a first correction parameter c and a second correction parameter a;
    adapting the corrected intensity spectrum $S'(c,a,\lambda)=c+a^*S(\lambda)$ to a reference spectrum $R(\lambda)$ in order to reduce a deviation, defined by a distance measure, which the corrected intensity spectrum $S'(c,a,\lambda)$ has from the reference spectrum $R(\lambda)$, there being ascertained through the adapting an adapted corrected intensity spectrum $S'(\lambda)=c^*+a^*\cdot S(\lambda)$ adapted to the reference spectrum, whose first correction parameter c assumes a value $c^*$ and whose second correction parameter a assumes a value $a^*$,
    calculating a distance which the adapted corrected intensity spectrum adapted to the reference spectrum has from the reference spectrum; and
    employing the calculated distance for assessing the similarity between the recorded intensity spectrum and the reference spectrum.

2. The method according to claim 1, wherein the first and second correction parameters are ascertained through the adapting of the linearly corrected intensity spectrum to the reference spectrum.

3. The method according to claim 1, wherein the adapting of the corrected intensity spectrum to the reference spectrum is carried out individually for each value document to be checked individually for each recorded intensity spectrum of each value document to be checked.

4. The method according to claim 1, wherein, through the adapting of the corrected intensity spectrum to the reference spectrum, fluctuations due to measuring technology that have influenced the recorded intensity spectrum upon its recording are compensated at least partly.

5. The method according to claim 1, wherein the adapting of the corrected intensity spectrum to the reference spectrum is carried out within the framework of a compensation calculation by which a least-squares fit of the corrected intensity spectrum to the reference spectrum is carried out.

6. The method according to claim 1, wherein the distance that is calculated between the adapted corrected intensity spectrum and the reference spectrum is the chessboard distance of the adapted corrected intensity spectrum from the reference spectrum.

7. The method according to claim 1, wherein by the method there is checked a spectral characteristic of a security feature of the value document for its similarity to a spectral characteristic specified for the security feature with which the security feature was specified before the value document was equipped with the security feature.

8. The method according to claim 7, wherein, for assessing the similarity of the recorded intensity spectrum to the reference spectrum, the calculated distance, in particular the chessboard distance, is compared with a specified fluctuation range with which the spectral characteristic of the security feature was specified.

9. The method according to claim 1, wherein the adapting of the corrected intensity spectrum to the reference spectrum is carried out in a spectral portion of the recorded intensity spectrum which comprises only wavelengths in the infrared.

10. The method according to claim 1, wherein, upon calculating the distance, the distance is calculated only for a partial portion of that spectral portion for which the adapting of the corrected intensity spectrum to the reference spectrum was carried out.

11. The method according to claim 1, wherein, upon calculating the distance, the distance is calculated only for a spectral portion of the adapted corrected intensity spectrum from the reference spectrum, in which the value document is checked for a spectral characteristic of a security feature, said spectral portion preferably lying completely in the infrared.

12. The method according to claim 1, wherein the adapting of the corrected intensity spectrum to the reference spectrum is carried out in a constrained manner such that the adapted corrected intensity spectrum is not falsified in comparison to the recorded intensity spectrum.

13. The method according to claim 1, wherein the adapting is carried out so as to be constrained by one or several certain side conditions being prescribed for two parameters derived from the first and second correction parameters.

14. A sensor for checking value documents which is configured for carrying out the method of claim 1.

15. An apparatus for checking value documents which has a sensor for checking value documents according to claim 14.

* * * * *